(12) United States Patent
Lashkari et al.

(10) Patent No.: US 6,350,031 B1
(45) Date of Patent: *Feb. 26, 2002

(54) ELECTRO-OPTIC BINOCULAR INDIRECT OPHTHALMOSCOPE

(76) Inventors: Kameran Lashkari, 330 Darthmouth St., Boston, MA (US) 02214; Mark Harooni, 33 Stepping Stone La., Kings Point, NY (US) 11024

( * ) Notice: Subject to any disclaimer, the term of this patent is extended or adjusted under 35 U.S.C. 154(b) by 0 days.

This patent is subject to a terminal disclaimer.

(21) Appl. No.: 09/595,554

(22) Filed: Jun. 15, 2000

Related U.S. Application Data

(63) Continuation of application No. 09/197,964, filed on Nov. 23, 1998, now Pat. No. 6,089,716, which is a continuation-in-part of application No. 08/681,713, filed on Jul. 29, 1996, now Pat. No. 5,841,509.

(51) Int. Cl.$^7$ .................................................. A61B 3/10
(52) U.S. Cl. ....................................................... 351/221
(58) Field of Search ................................. 351/205, 206, 351/200, 209, 210, 211, 212, 221, 246

(56) References Cited

U.S. PATENT DOCUMENTS

| | | | |
|---|---|---|---|
| 3,403,957 A | 10/1968 | Wilkinson et al. | 351/38 |
| 3,582,191 A | 6/1971 | Cohen et al. | |
| 3,685,887 A | 8/1972 | Spurney | |
| 3,847,470 A | 11/1974 | Dederer et al. | |

(List continued on next page.)

FOREIGN PATENT DOCUMENTS

| | | |
|---|---|---|
| DE | 3737935 | 5/1989 |
| EP | 0048181 A2 | 3/1982 |
| EP | 048181 | 3/1982 |
| WO | WO 9920056 | 4/1999 |

OTHER PUBLICATIONS

Mainster et al, "Scanning Laser Ophthalmoscopy: Clinical applications," *Ophthalmology*, 89: 852–857 (1982).
Eli Peli, "Electro–Optic Fundus Imaging," *Survey of Ophthalmology*, vol. 34, No. 2, Sep.–Oct. 1989, pp. 113–121.
Perlstein Et Al., "New Techniques in Fundus Examination: II. A New Look Simplified Technique for Binocular Indirect Ophthalmoscopy," *Annals of Ophthalmology*, Jan. 1983, pp. 86–87.
Perlstein Et Al., "New Techniques in Fundus Examination: I Simplified Binocular Fundus–Lens Indirect Ophthalmoscopy," *Annals of Ophthalmology*, Dec. 1982, pp. 1141–1142.
Snead Et Al., "The Optics of Fundus Examination," *Surv. Ophthalmol.* vol. 36, pp. 439–445, 1992.

*Primary Examiner*—George Manuel
(74) *Attorney, Agent, or Firm*—Foley, Hoag Eliot LLP

(57) ABSTRACT

The present invention relates to a binocular indirect ophthalmoscope for observing and examining the fundus of the human eye. The ophthalmoscope of the invention integrates an electro-optic imaging system in the viewing optics of the ophthalmoscope. Advantageously, such integration permits the stereoscopic observation of the retina and choroid by employing radiation ranging from the near ultraviolet to the infrared, including the visible spectrum. A light source illuminates a desired portion of a patient's fundus and the radiation reflected in response to the illuminating radiation is brought to focus to produce an aerial image of the fundus. A pair of ophthalmoscope lenses then magnify and image the aerial image along two different optical paths onto imaging sensors, such as charge coupled devices (CCDs) and image cameras, or image tubes such as image intensifiers. Visible displays, such as liquid crystal displays (LCDs), cathode ray tubes (CRTs), or the fluorescent screen of the image tube, then photoelectrically convert the fundus images formed on the imaging sensors and direct corresponding visible images thereof to an observer's pupils by means of ocular lenses.

78 Claims, 14 Drawing Sheets

U.S. PATENT DOCUMENTS

| | | |
|---|---|---|
| 3,881,812 A | 5/1975 | Ben-Tovim |
| 3,963,329 A | 6/1976 | Stumpf et al. |
| 4,015,898 A | 4/1977 | Schirmer |
| 4,056,310 A | 11/1977 | Shimizu |
| 4,166,677 A | 9/1979 | Heine et al. |
| 4,279,478 A | 7/1981 | Matsumura .................. 351/13 |
| 4,331,392 A | 5/1982 | Sato |
| 4,449,797 A | 5/1984 | Kocher et al. |
| 4,469,413 A | 9/1984 | Shirayanagi |
| 4,514,476 A | 4/1985 | Fitzgerald |
| 4,538,888 A | 9/1985 | Sigelman |
| 4,568,158 A | 2/1986 | Blaha et al. |
| 4,580,559 A | 4/1986 | L'Esperance |
| 4,637,699 A | 1/1987 | Sigelman |
| 4,669,837 A | 6/1987 | Schirmer et al. |
| 4,671,631 A | 6/1987 | Sigelman |
| 4,682,866 A | 7/1987 | Volk |
| 4,684,227 A | 8/1987 | Schmidt et al. |
| 4,721,378 A | 1/1988 | Volk |
| 4,738,521 A | 4/1988 | Volk |
| 4,810,083 A | 3/1989 | Okada et al. |
| 4,838,678 A | 6/1989 | Hubertus |
| 5,200,773 A | 4/1993 | Volk |
| 5,223,863 A | 6/1993 | Heine et al. |
| 5,225,859 A | 7/1993 | Fleischman .................. 351/206 |
| 5,252,999 A | 10/1993 | Sukigara et al. |
| 5,255,025 A | 10/1993 | Volk |
| 5,333,017 A | 7/1994 | Volk |
| 5,333,018 A | 7/1994 | Heine et al. |
| 5,394,201 A | 2/1995 | Hauptli |
| 5,400,092 A | 3/1995 | Shepens et al. ............. 351/214 |
| 5,430,506 A | 7/1995 | Volk |
| 5,436,680 A | 7/1995 | Volk |
| 5,479,222 A | 12/1995 | Volk |
| 5,557,349 A | 9/1996 | Yoneya ...................... 351/206 |

ELECTRO-OPTIC BINOCULAR INDIRECT OPHTHALMOSCOPE

RELATED APPLICATION

This application is a continuation of U.S. patent application Ser. No. 09/197,964, filed Nov. 23, 1998, now U.S. Pat. No. 6,089,716, incorporated by reference herein in its entirety, which is a continuation-in-part of U.S. patent application Ser. No. 08/681,713, filed Jul. 29, 1996 now U.S. Pat. No. 5,841,509.

FIELD OF THE INVENTION

The present invention relates to ophthalmoscopes and, more particularly, to binocular indirect ophthalmoscopes for observing and examining the fundus oculi of human eyes.

BACKGROUND OF THE INVENTION

Binocular indirect ophthalmoscopy offers several advantages over direct ophthalmoscopy, including stereopsis and a much enlarged field of view and depth of field. However, the usefulness and flexibility of binocular indirect ophthalmoscopy has been generally restricted to use in the examination of eyes with substantially clear opacity. Other techniques using infrared scanning laser ophthalmoscopes or infrared fundus cameras are generally employed to examine eyes with media opacity.

For example, scanning laser ophthalmoscopy (SLO) using infrared illumination is preferably used to examine eyes with nuclear sclerotic cataracts or mild vitreous hemorrhage, and in combination with indocyanine green angiography (ICG) to examine the choroidal layer, lesions and subretinal membranes and scars of the eye. SLO uses a low power, focused laser beam, typically Helium-Neon ("He—Ne"), to scan the size of the aperture through which the reflected radiation is collected. The advantages of SLOs as well as those of infrared fundus cameras are well known to those skilled in the art. Unfortunately, SLOs as well as infrared fundus cameras are prohibitively costly for most clinicians and lack the accustomed stereopsis, which is helpful in evaluating the topography of the fundus features. For these reasons, a need has arisen for an improved binocular indirect ophthalmoscope having comparable capabilities to those of SLOs or infrared fundus cameras, but yet which is relatively inexpensive.

SUMMARY OF THE INVENTION

An improved binocular indirect ophthalmoscope for observing and examining the fundus of the human eye is realized by integrating an electro-optic imaging system in the viewing optics of the ophthalmoscope. Advantageously, this permits the direct stereoscopic observation of the fundus using illumination ranging from the near ultraviolet to the infrared, including the visible spectrum.

In accordance with the principles of the present invention, a radiation source illuminates a desired portion of a patient's fundus, with the reflected radiation brought to focus to produce an aerial image of the fundus. A pair of ophthalmoscope lenses then magnify and image along two different optical paths the aerial image onto separate imaging sensors, such as charge coupled devices (CCDs) or camera tubes, or onto image tubes such as image intensifiers, and the like. For CCDs and camera tubes, visible displays, such as liquid crystal displays (LCDs) or cathode ray tubes (CRTs), then photo-electrically convert the fundus images formed on the imaging sensors and direct corresponding visible images thereof to an observer's pupils by means of ocular lenses. Of course for image tubes, the observed visible display results when electrons emitted by the photosensitive surface of the image tube strike its fluorescent screen which reproduces the fundus image focused on the photosensitive surface.

Although not limited to, both visible and infrared imaging are readily available by judiciously selecting the spectral characteristics of the radiation source, filters and imaging sensors of the present ophthalmoscope. This is a particularly distinct advantage over prior art binocular indirect ophthalmoscopes which can only operate in the visible spectrum.

The electro-optical indirect ophthalmoscope of the invention is well suited for performing retinal angiography and for assessment of retinal circulation. One practice of the invention places filters in the excitation and detection paths of the ophthalmoscope to perform fluorescein or infrared angiography. For example, excitation of a fluorescein dye, applied to a subject's eye, in the blue portion of the electromagnetic spectrum elicits fluorescence from the eye in the green portion of the spectrum. Thus, placement of appropriate filters in the excitation and detection paths allows performing such a fluorescein angiography. An alternative practice of the invention excites an indocyanine green dye by near infrared radiation, and detects the fluorescence of the dye at a slightly longer wavelength than that of the infrared excitation, e.g., at 810 nanometers.

Another feature of the ophthalmoscope of the invention is its capability to perform angiography of the peripheral retina of a subject. In particular, the present phthalmoscope can provide viewing of the far periphery of the subject's retina to document vascular changes. In contrast, a conventional fundus camera provides much more limited range for the examination of the subject's retina, typically up to approximately 50 degrees across the periphery of the retina. Thus, the present ophthalmoscope can detect retinal lesions that may be missed by a fundus camera.

A further aspect of the indirect ophthalmoscope of the invention relates to the projection of images, shapes, and/or letters onto the retina of a subject. One practice of the invention forms such images on the subject's retina by projecting light onto the subject's retina after passing the light through an image former, such as a sliver glass having an imprint of the image thereon. In some preferred embodiments, the source of light for projecting an image onto the subject's retina is, for example, a laser such as a He—Ne laser having a power output that is safe for the eye. A variety of different images such as those of the Snellen visual acuity chart, or cartoon images can be employed. The projection of an image onto the subject's retina provides a fixation target for the subject to follow as an examiner moves the image to observe various portions of the retina. The fixation target in conjunction with other elements of the ophthalmoscope of the invention allows detailed examination of the periphery of the subject's retina. In particular, moving the target image to extreme ranges of the subject's gaze allows examination of the peripheral retina.

The fixation target allows, among other applications, estimation of the subject's visual acuity by projection of Snellen letters onto the subject's retina, assessment of macular function and the pattern of foveal fixation on target, and the study of the preferred extra-foveal retinal locus of fixation in subjects with macular diseases such an age-related macular degeneration. In addition, the fixation target allows mapping of the center of fixation, which is useful for example in preparation for laser photocoagulation of the retina near the center of macula in conjunction with retinal angiography performed with the ophthalmoscope of the invention. The presence of a fixation target in the indirect ophthalmoscope of the invention is particularly useful in pediatric ophthalmology. Children are typically photophobic, and hence are difficult to examine. The fixation target allows projecting an image, for example a cartoon image, onto the child's retina to assess the behavior of the fixation and macular function.

According to another aspect of the invention, a computer collects the data corresponding to the images of the subject's retina obtained through the practice of the invention. A software program allows selected manipulation of the collected data. For instance, digital images of the retina can be enhanced according to known digital processing methods. Alternatively, different retinal images can be added together or subtracted from each other to obtain structural information and/or enhance visualization of certain features of the retina.

One aspect of the invention relates to obtaining images of the same portion of a subject's retina by employing radiation in different regions of the electromagnetic spectrum. For example, four images can be obtained of the same retinal area by employing light in the blue, green, yellow, and the red regions of the spectrum. The images can be digitized and the digital data transferred to a software program. The program can, for example, obtain the difference between the intensity of the blue image and the red image to provide information regarding the subject's retinal thickness. Alternatively, the difference between the blue and the green images provides information regarding the subject's inner retinal thickness. In an alternative practice of the invention, the four images with different wavelengths, can be displayed in rapid succession on a monitor to provide the examiner with a three-dimensional image that approximately correlates with the retinal topography.

These and other features of the invention are more fully set forth below with reference to the detailed description of the invention, and the accompanying figures.

BRIEF DESCRIPTION OF THE DRAWINGS

A more complete understanding of the invention may be obtained by reading the following description in conjunction with the appended drawing in which like elements are labeled similarly and in which.

DESCRIPTION OF ILLUSTRATED EMBODIMENTS

The ophthalmoscope of the invention, which integrates an electro-optic imaging system in the viewing optics of an ophthalmoscope, allows the direct stereoscopic observation of the fundus of the human eye by employing illuminating radiation from the near ultraviolet to the infrared. Such electro-optic imaging systems include the use of CCDs, CRTs, LCDs, camera tubes and image tubes. Where the fundus is displayed as a video image, well known digital image processing techniques may be optionally used to delineate and enhance desired features of the fundus image in real-time, including those techniques used, for example, in SLOs. Such digital image processing techniques, among others, may include scaling, rotating, pseudo-coloring or feature extracting of the fundus image.

The present invention provides comparable visualization as SLOs which are prohibitively costly for most clinicians and lack stereopsis, which is particularly important to measure depth and evaluate the topography of retinal features, such as the optic nerve head and peripheral retina. Moreover, the present ophthalmoscope allows real-time visualization of the fundus.

Without any loss of generality of or applicability for the principles of the present invention, the descriptions of some embodiments are with respect to conventional imaging and illumination optics. It should, however, be clearly understood that the present invention is equally applicable to other types of imaging and illumination optics too numerous to discuss herein, which are well known in the art. Such alternative optics may be used, for example, to reduce the weight of the ophthalmoscope, provide a greater field of view, minimize aberrations and/or improve image quality. See in general, Born et al., *Principles of Optics: Electromagnetic Theory of Propagation, Interference and Diffraction of Light*, Pergamon Press, New York (1975).

It should also be clearly understood that direct ophthalmoscopes can similarly employ the electro-optic imaging system of the present invention, if a binocular image is not necessary.

Figure 1:
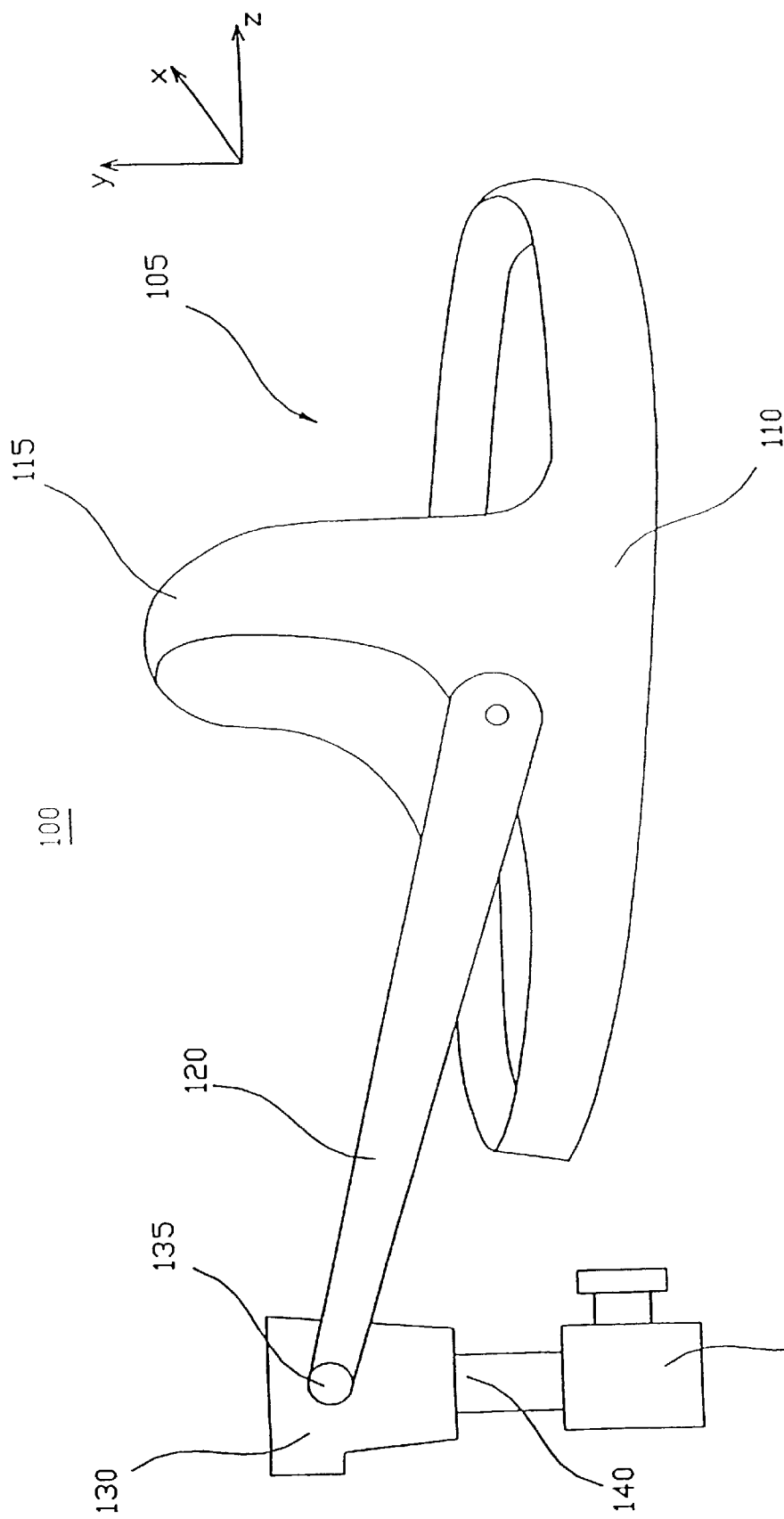
FIG. 1 is plan elevation view of a binocular indirect ophthalmoscope in accordance with the principles of the invention.
Figure 2:
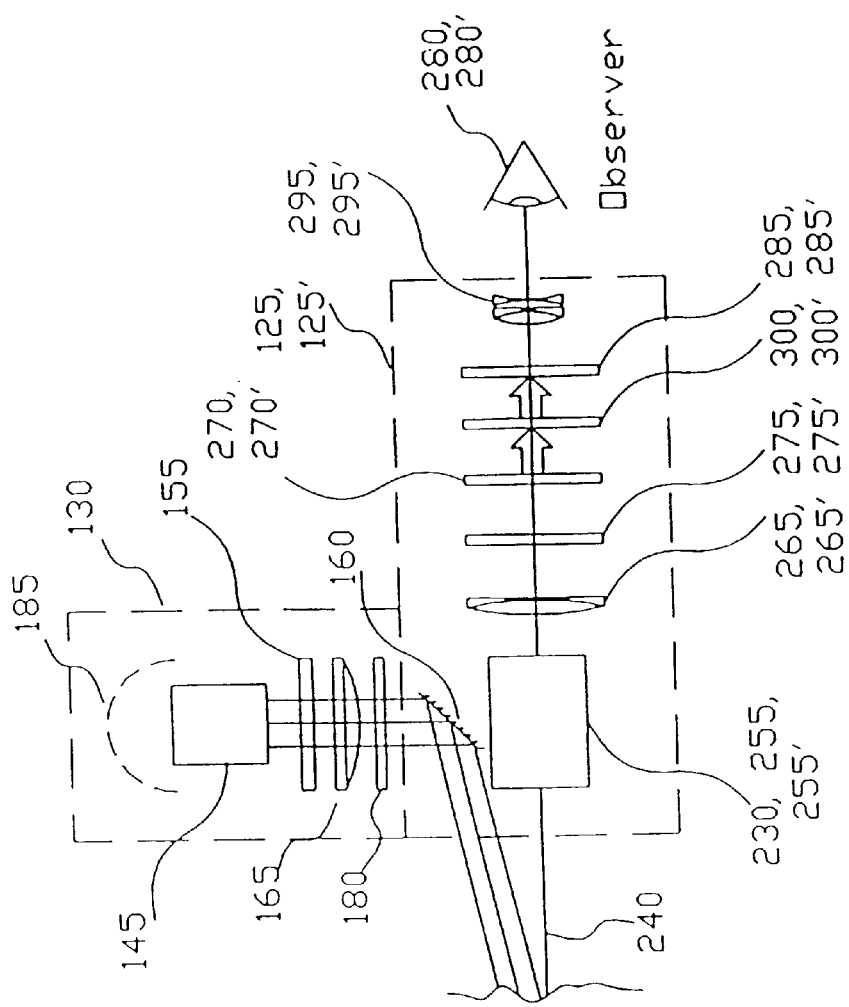
FIG. 2 is a schematic plan view of the illumination assembly of the binocular indirect ophthalmoscope of FIG. 1.
Figure 2:
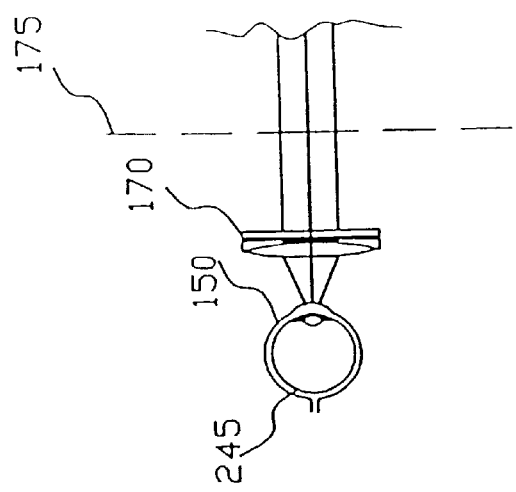
Figure 2:
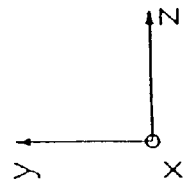
Figure 3:
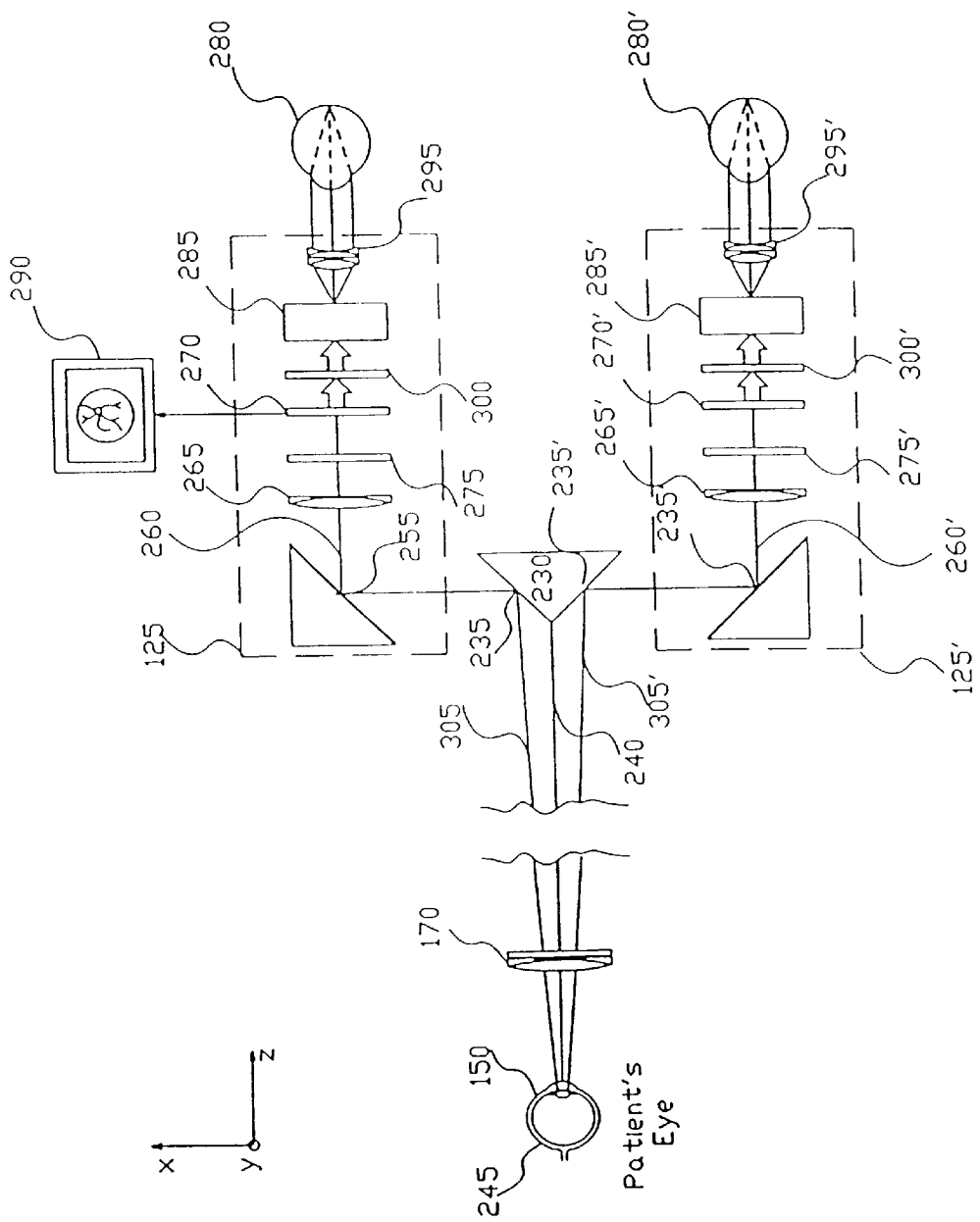
FIG. 3 is a schematic plan view of the viewing assembly of the binocular indirect ophthalmoscope of FIG. 1.
Figure 4A:
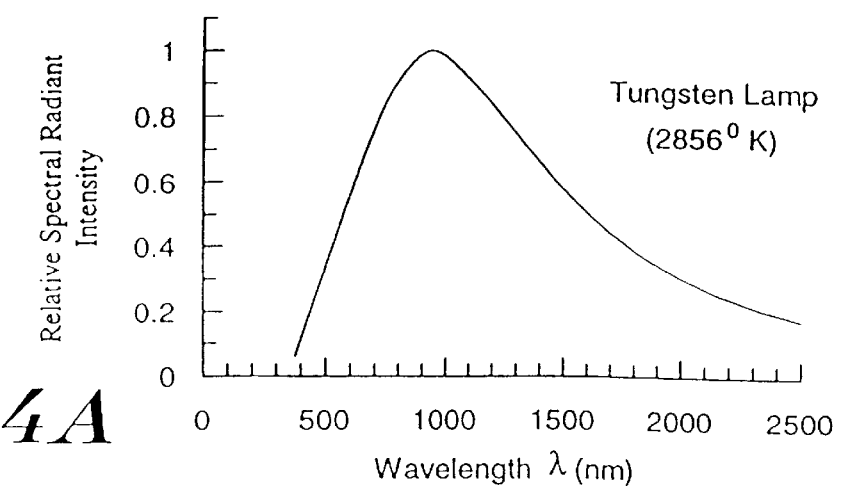
FIGS. 4(a)–(d) depict the spectral characteristics of a variety of light sources which may be used in the binocular indirect ophthalmoscope of the present invention.
Figure 4B:
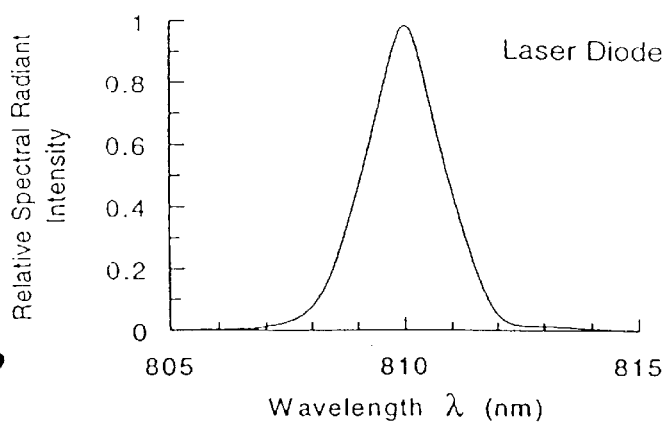
Figure 4C:
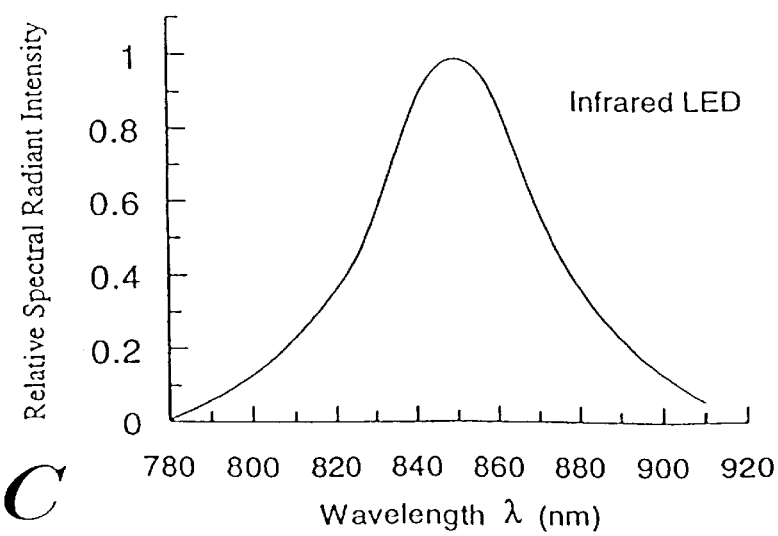
Figure 4D:
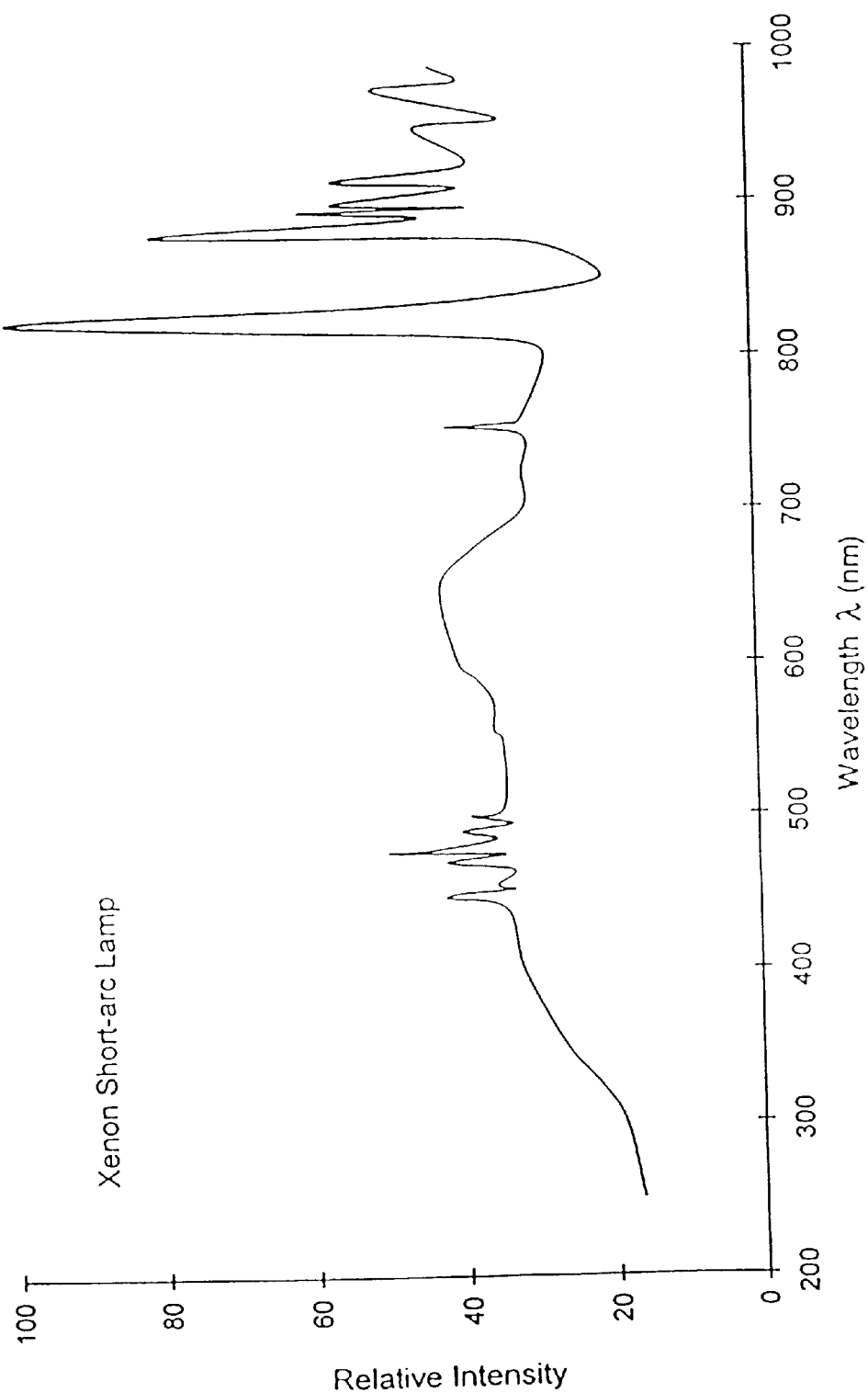

Referring to FIGS. 1–3, there is shown an exemplary embodiment of a binocular indirect ophthalmoscope 100 in accordance with the principles of the present invention. Ophthalmoscope 100, which includes an adjustable head assembly 105, may be worn on the head of a clinician using the ophthalmoscope in a manner similar to a conventional indirect ophthalmoscope. Head assembly 105 may have a head band 110 for encircling the head, a strap 115 integral with head band 110 adapted to fit on top of the head, and a semi-circular band 120 pivotally attached to the sides of the head band 110 and extending toward the front end thereof. Viewing assemblies 125, 125' below an illumination assembly 130 may be secured to the forward part of semi-circular band 120 by a coupling attachment 135 or other suitable means. Although the semi-circular band 120 is rigidly secured, it may be pivoted up or down with reference to head band 110 so as to adjust the vertical position of viewing assemblies 125, 125'.

The housing of illumination assembly 130 has a tube 140 or other similar means extending downwardly therefrom into viewing assemblies 125, 125' which is provided with means therein for permitting binocular vision when the observer's eyes are optically aligned with viewing assemblies 125, 125', as discussed herein below. Illumination assembly 130 includes one or more light source(s) 145, such as a bulb, light emitting diode (LED), laser, laser diode or the like, emitting in a predetermined radiation spectrum and connected to a power source of sufficient voltage to operate the source. Of course, multiple light sources may be used, depending on the desired application. In some preferred embodiments, the illumination assembly may also include a light source, such as a He—Ne laser, and a fixation target such as a silver glass having an imprint of an image thereon for projecting the imprinted image onto the subject's retina.

It should be clearly understood that a judicious selection of the spectral characteristics of the light source 145 and/or the bandpass region of an optical filter(s) 155 positioned, for example, after the light source 145 tailors the spectral characteristics of the illuminating radiation directed to the patient's pupil 150 to a desired application. Although not limited to, both visible and infrared imaging are readily selectable. This is a particularly distinct advantage over prior art binocular indirect ophthalmoscopes which only operate in the visible spectrum. It is important to understand, for example, that infrared radiation is particularly well suited for examining eyes with opacities, including nuclear sclerotic cataracts or vitreous hemorrhage. Infrared light generally penetrates such opacities more efficiently than visible radiation, allowing a visualization of otherwise obscured structures. Infrared light also penetrates the retina itself, allowing the choroidal neovascular membrane to be imaged, which is very difficult to do with conventional indirect ophthalmoscopes. Other radiation wavelengths, of course, may be better suited to view other features of the fundus.

Accordingly, one practice of the invention designs the optical filter 155, for example, to selectively pass visible radiation in the range of about 400–700 nm, or near infrared radiation in the range of about 750–900 nm. Of course, discrete radiation wavelengths—in the visible and/or infrared spectrum—may also be spectrally selected. For example, those skilled in the art will readily recognize the advantages of using the radiation wavelength of 805 nm for ICG. In general, using infrared illumination results in higher contrast and better visualization for certain features, including the choroidal layer, lesions, subretinal membranes and scars of the eye.

Optical filter 155 may comprise absorption bandpass filters and/or interference filters, as well as narrow bandpass filters, which are all well known in the art. For narrow wavelength band light sources, such as lasers, which typically emit a single discrete radiation wavelength, the need for optical filter 155 in illumination assembly 130 is obviously obviated. Such filters, however, may still be employed in the viewing assemblies so as to eliminate any unwanted radiation from other sources, as discussed herein below.

Shown in FIG. 4 are typical plots of the spectral characteristics of several light sources that may be used for the light source 145. Xenon, argon, tungsten lamps and the like may be used to provide broad band radiation from the visible through the infrared spectrum. Semiconductor lasers or LEDS, however, including those using $In_xGa_{1-x}As$, $InP_xAs_{1-x}$, $Al_xGa_{1-x}As$ and $GaAs_{1-x}P$, among others, are more particularly well suited for providing near infrared radiation (750–900 nm). Preferably, light source 145 emits radiation over a broad spectrum from the visible to the infrared or at one or more discrete wavelength(s) in the infrared spectrum.

Now referring back to FIGS. 1–3, an illumination mirror 160 is used to direct radiation from the light source 145 which is exiting through a condenser 165 to the patient's eye. Reflective elements, such as multilayer mirrors, may be used to reflect only the radiation wavelengths of interest to the patient's pupil, dispensing with the need for optical filter 155. Gold-coated mirrors are preferably employed through the infrared spectrum. Such mirrors only have a high reflectivity above 500 nm, and as such fortuitously filter out any short wavelength radiation which may be harmful to the eye.

Figure 2A:
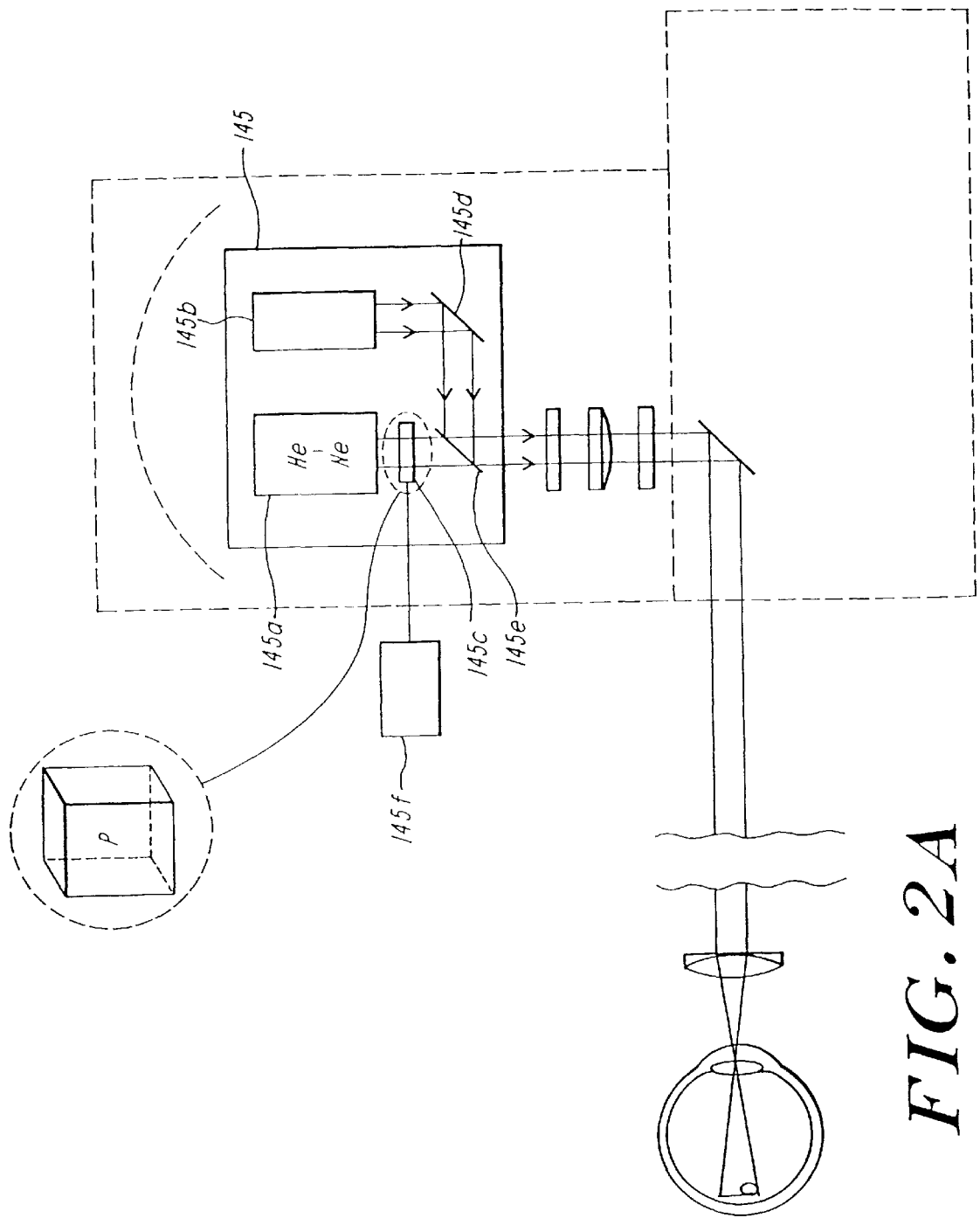
FIG. 2a is a schematic plan view of a portion of a binocular indirect ophthalmoscope according to the invention having a fixation target.

The light source 145 may optionally include a low-power He—Ne laser for projecting an image onto the subject's retina to provide a fixation target for the subject to follow. FIG. 2a illustrates this aspect of the invention. In particular, reference to FIG. 2a shows a light source 145a, such as a He—Ne laser, and a silver glass 145c on which an image, such as the letter P, is imprinted. The light from the Ne—Ne laser 145a passes through the silver glass 145c, thus bearing the imprint of the letter P. A separate light source 145b, such as an infrared light source, provides the radiation to be directed to the patient's eye for examination purposes. A mirror 145d, such as a gold-coated mirror, reflects the infrared radiation toward an optical beam conditioner 145e that can be, for example, a piece of glass that is transparent to the visible radiation of the He—Ne laser 145a, and has a dielectric coating on its surface facing the radiation from the infrared source 145b. This dielectric coating is selected in a manner known in the art to reflect infrared radiation while being transparent to visible radiation. Thus, the passage of the visible light of He—Ne laser 145a through the optical beam conditioner 145e and the reflection of the infrared radiation emanating from the source 145b from a surface of the optical beam conditioner 145e provide two co-axial beams of light propagating toward the patient's eye. If both sources 145a and 145b emit visible radiation, the optical beam conditioner 145e can be a piece of glass having a thin coating of silver on one surface to allow the passage of the radiation from the source 145a, and to reflect the radiation from the source 145b toward the subject's retina along a co-axial path. Other methods of co-axially aligning two optical beams are known in the art and can be employed in the present ophthalmoscope.

The light from the He—Ne laser 145a forms an image of the letter P on the patient's retina, providing a fixation target for the patient to follow as the examiner moves the image to observe various portions of the patient's retina. A drive mechanism 145f, attached to the silver glass 145c, allows the examiner to move the fixation target horizontally and vertically in a manner known in the art. In particular, the examiner can move the target image to the extremes of the patient's gaze, thus allowing examination of the peripheral retina.

Referring again to FIGS. 1–3, those skilled in the art will readily note that an ophthalmoscopic lens 170 images light source 145 to the patient's pupil 150. As discussed herein below, ophthalmoscopic lens 170 is held close to the patient's eye and provides an image of the patient's retina from light reflected back from the fundus. An ophthalmoscopic lens of about 15–80 diopters may be used as lens 170. A high power lens typically results in a low image magnification, but a larger field of view. In an emmetropic system, a real image (aerial image) is formed at a focal plane 175 of ophthalmoscopic lens 170. The lens 170 is of sufficiently good optical quality to generate an image of the fundus with an acceptable image resolution. Lens 170, of course, may be fabricated to be selectively transmissive within a desired spectral range, thereby functioning not only as a lens but also as a filter.

Figure 5:
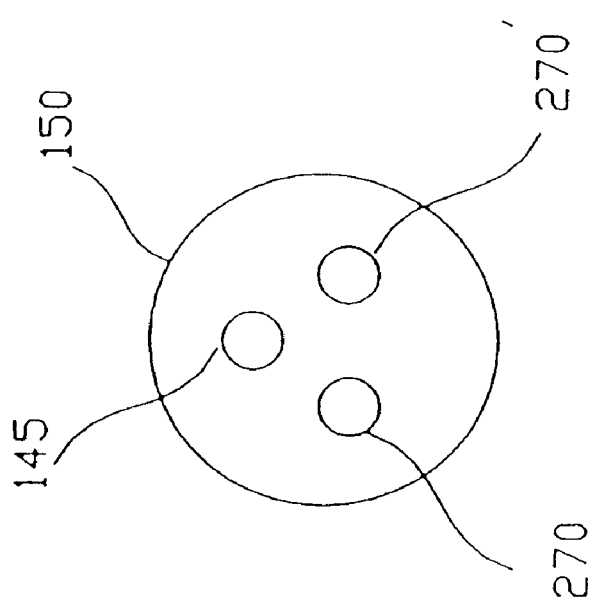
FIG. 5 is an illustrative diagram depicting the position of the imaging sensors and the light source in the patient's pupil.

Illumination mirror 160 may be moved independently of viewing assemblies 125, 125' located underneath it. Alternatively, illumination mirror 160 may be fixedly mounted with respect to the viewing assemblies to move with it. Regardless of the illumination type, an image of illumination source 145 is produced at the patient's pupil along with the images of the imaging sensors, as illustrated in FIG. 5, and discussed herein below.

Radiation from light source 145 may be optionally directed through an illumination diaphragm 180. If desired, a hemispherical reflector 185 may also be mounted in the rear of light source 145 to effectively concentrate the light through diaphragm 180. Likewise, hemispherical reflector 185 may be selectively reflective within a desired spectral range so as to tailor the radiation spectrum of the illumination. Alternatively, the amount of visible as well as infrared radiation directed to the anterior part and retina of the patient's eye may be adjusted to within safe levels through the use of neutral density filters, for example, positioned between the light source and condenser. Or, the intensity of light source 145 may be adjusted by controlling the bias voltage thereto.

For visible radiation, the retina may be safely exposed to illumination levels of about 100–150 mW/cm$^2$. See, for example, Mainster et al., *Ophthalmology*, Vol. 89, pp. 852–857 (1982). At radiation wavelengths near about 800 nm, illumination levels of about 500–600 mW/cm$^2$ are believed to be safe. See, for example, Sliney et al., "Hazard Analysis of Broadband Optical Source," U.S. Army Environmental Hygiene Agency. In general, the absorption is much lower for near infrared radiation than for visible. As such, it is believed that for the same level of illumination, the eye is less likely to be harmed with near infrared radiation. Furthermore, the use of high gain imaging sensors permits lower illumination levels to be used.

Nevertheless, to minimize the exposure of the eye to harmful radiation while maintaining adequate brightness, one practice of the invention employs a pulsed light source that is synchronized with the beginning of a video frame, if the visible display is a video image. Typically, for pulsed radiation, the safe limits of illumination are much greater than those for continuous radiation. Pulses as short as 1/100th of a second or less may be used with imaging sensors having a long persistence duration. Although such a time period is shorter than one video frame (1/30th of a second), the flashed or pulsed illumination still allows a full image to be displayed because of the relatively slow decay of the imaging sensor. The flashed illumination results in an "after image" on the imaging sensors that can be obtained even after the illumination has been extinguished. Of course, since the image decay starts as soon as the flashed illumination disappears, the amount of decay needs to be corrected so that the bottom of the video image remains as bright and with comparable contrast as the top. For example, automatic gain control may be used for such corrections.

To insulate the observer from heat generated by light source 145, such as a filament type source, a laminated tunfnol layer of about a few millimeters or other suitable heat insulator may be positioned between the housing of light source 145 and its outside frame. The intensity of the illumination light can then be adjusted by limiting the aperture of illumination diaphragm 180. Alternatively, the light source itself may be separated from the ophthalmoscope and connected thereto through an optical fiber, as discussed herein below.

Alternatively, a prism (not shown) may be used with condenser 165 to direct the illumination from the higher disposed light source to the lower disposed level of the viewing axis. In this latter case, the illumination will then be refracted downward by the prism to intersect the viewing axis. In this latter instance, illumination mirror 160 is not necessary. Other types of illumination techniques may also be used, such as, for example, slit beam illumination, retro-illumination and the like. See, for example, U.S. Pat. No. 3,403,957, which is incorporated herein by reference.

Figure 6:
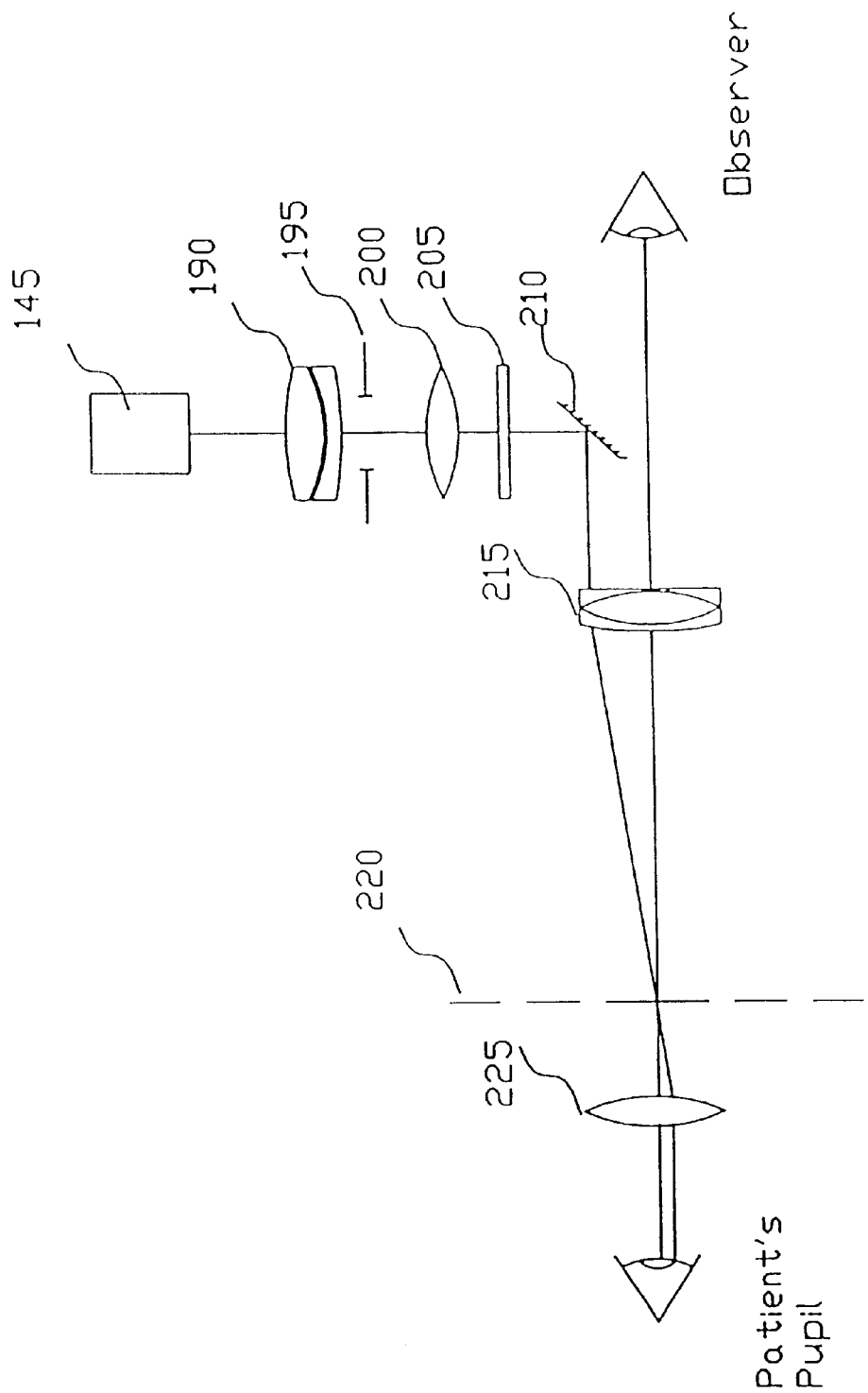
FIG. 6 is a diagram of an alternative illumination system which may be used with the binocular indirect ophthalmoscope of the present invention.

Alternatively, the illumination system of Schepens et al., for example, may also be used as shown in FIG. 6. In this latter case, radiation from light source 145 is collimated by a condensing lens 190, passes through diaphragm 195 and is focused in the plane of optical filter 205. Diaphragm 195 is located at the focal plane of an objective lens 200. The light is reflected further by mirror 210 and passes through teleocentric ocular lens 215, forming an image of diaphragm 195 in an image plane 220. After passing through ophthalmoscopic lens 225, the light is focused in the pupil plane of the patient's eye. By changing ocular lens 215, it is possible to change the illumination diameter in image plane 220 without changing the light power. Advantageously, this type of illumination provides a uniform illumination for different magnifications and reduces the illumination pupil diameter in the patient's pupil plane. See, U.S. Pat. No. 5,400,092, which is incorporated herein by reference.

Referring specifically to FIG. 3, viewing assemblies 125, 125' include a mirror assembly 230 having, for example, two reflective surfaces, 235, 235' at approximately 45° to the viewing direction along an optical axis 240. This angle, however, may be adjusted to obtain the best stereopsis. Preferably, mirror assembly 230 is movable over a short distance—about 3 mm—in a direction parallel to optical axis 240 of the ophthalmoscope. This alters the length of the stereo base of the ophthalmoscope. Alternatively, each reflective surface may be replaced with a prism.

Incoming light rays emanating from the fundus of eye 245, in response to the illuminating radiation, propagate through ophthalmoscopic lens 170, strike reflective surfaces 235, 235', and then are directed laterally onto a second pair of mirrors 255, 255', respectively. One preferred practice of the invention mounts each mirror such that its angle of rotation is adjustable to allow easy realignment of the mirror in the event that the mirror becomes misaligned. Mirrors 255, 255' may be in form of a prism, such as a Schmidt or Pechan prisrm that shortens the length of system by folding the rays of the light within the prism. At the same time, such prisms can re-invert the aerial image without interfering with the optical axis. Such re-inversion of the aerial image is not necessary, but may be optionally desirable.

Mirrors 255, 255' provide two optical paths, 260, 260' corresponding to viewing axes 305, 305' which are at a non-zero angle to each other (~15°) and are also at a nonzero angle to optical axis 240. Presenting the fundus image to the observer along two different viewing axes advantageously provides a binocular image in a manner similar to conventional ophthalmoscopes. Mirrors 255, 255' reflect the light rays through lens 265, 265', respectively, which focus onto imaging sensors 270, 270' an image of the aerial image of the patient's eye. The mirrors 255, 255' as well as others in the present ophthalmoscope may be gold coated for use with radiation wavelengths from the visible through the infrared spectrum. Optionally, the optical filters 275, 275' may be positioned in front of the imaging sensors 270, 270' to pass only the radiation having wavelengths of interest, so as to provide improved image quality.

Alternatively, an optical filter(s) may be positioned in front of mirror assembly 230, instead of using filters 155, 275, 275'. In this latter case, those skilled in the art will readily note that both the illumination and reflected radiation propagate through the same optical filter positioned in front of mirror assembly 230.

Typically, the spectral characteristics of optical filters 275, 275' are chosen to be comparable to those of optical filter 155, if present. One exception, however, is when it is desirable to collect the fluorescence of the retina, such as for ICG. In this latter case, the retina, which has been subjected to a specific dye, is illuminated by a particular wavelength to cause the dye to fluoresce, and is viewed using a different radiation wavelength to detect the fluorescence thereof. The fluorescence can be a native fluorescence of the tissues or the fluorescence of the dye used to selectively color some detail of the eye. For example, excitation of a fluorescein dye in the blue portion of the visible spectrum causes the dye to fluoresce in the green portion of the spectrum. In such a case, the filter 155 can be selected to pass the blue excitation light, and the filters 275, 275' selected to pass the green fluorescence light. Alternatively, an indocyanine dye can be excited by near infrared radiation to fluoresce in a slightly longer wavelength than the excitation wavelength. Regardless, imaging sensors 270, 270' should be particularly sensitive to the radiation wavelengths of interest for the desired application, typically from the visible through the infrared spectrum.

View assemblies 125, 125' are each slidably movable so as to be spaced apart from each other to permit the adjustment of the spacing between pupils 280, 280' of the observer. Typically, the interpupillary distance ranges between 56–72 mm.

The imaging sensors 270, 270' may be solid state CCDs or camera tubes, such as those found in video cameras, which are sufficiently sensitive to the radiation wavelengths of interest, including the near infrared spectrum. Other suitable devices, intensifiers suitable for night vision, may be used, thereby combining in a single device, imaging sensors 270, 270' and visible displays 285, 285', as discussed herein below.

Image intensifiers are image tubes that reproduce on a fluorescent screen an image of the radiation pattern focused on its photosensitive surface. Typically, a first generation image intensifier includes a photocathode (imaging sensor) upon which a radiant image is focused, an electron lens, and a fluorescent screen (visible display) upon which the output is displayed. Such image tubes may be used to convert non-visible radiation from an image into a visible display or to produce an image that is brighter than the input image. One practice of the invention employs suitable image intensifiers that are preferably of a second or third generation type which do not use an electron lens. Such image intensifiers, however, employ micro-channel plates having an automatic gain setting responsive to the illumination of the incident light.

Those skilled in the art will readily note that CCDs, unlike camera tubes, are solid state imaging devices which do not require a scanning beam. Such devices are capable of producing a video image display through the use of an external display, such as a LCD or a CRT. Individual cells of the CCDs are formed into a TV-type raster by an array of parallel conducting strips and channel stops at right angles thereto. In operation, electron-holes pairs are created when light is incident on the cells. Charges representing the picture element signals are stored in potential wells under biased electrodes. The charges are transferred by applying a pulse voltage to the electrodes with the image transferred in this manner to a storage raster during the vertical blanking period. Each horizontal line is then read out from the storage raster sequentially in a similar manner to provide, for example, a video signal. This video signal then may be displayed as an image on a LCD, CRT and the like.

FIG. 7 shows typical plots of the spectral responsivity of CCDs and image intensifiers. FIG. 7(*a*) labels each curve of FIG. 7, for illustrative purposes, with the image intensifier model number from Hamamatsu, Inc. having that spectral response. As noted, CCDs are typically sensitive to visible radiation up to and including the infrared spectrum near 1100 nm. The photocathodes of the image intensifiers, however, may be judiciously selected to be particularly sensitive to longer wavelength infrared radiation as well as visible radiation. Of course, the practice of the invention can employ various photocathode materials which have the desired spectral responsivities, ranging from the near ultraviolet to the infrared spectrum.

Preferably, such electro-optic imaging systems should have a resolution at least sufficient to resolve details in the vascular pattern of the patient's fundus for examination purposes, such as 10–30 line pairs/mm. The imaging sensors can be selected to obtain both black and white as well as color images. For example, color CCDs are readily available in sizes of ⅓–1" diameters and are capable of providing real-time color images. Also, various camera tubes as well as image intensifiers are readily available from different manufacturers, such as from Hamamatsu, Inc. Japan, or Delft Electroniache Producten, Netherlands, among others. In particular, image intensifier model no. XX1451-J from Delft Electroniache Producten, may be used in the present ophthalmoscope.

Figure 7A:
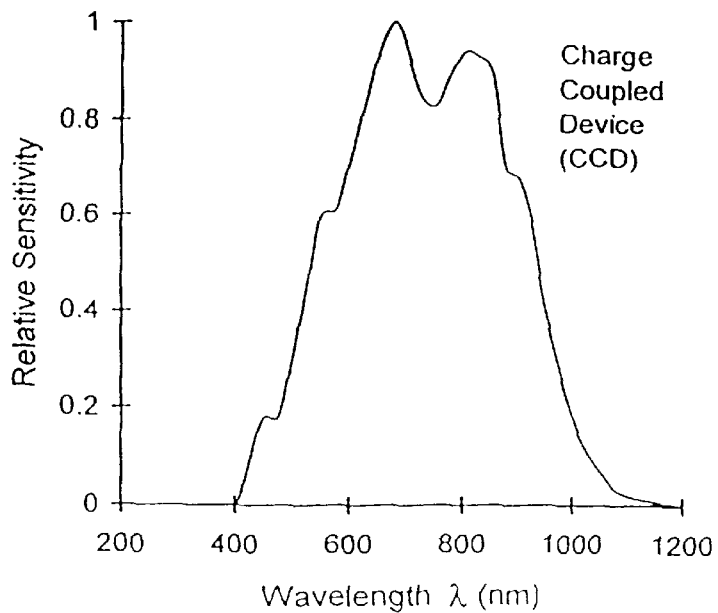
FIGS. 7(a)–(b) depict the spectral responsivities of a variety of imaging sensors which may be used in the binocular indirect ophthalmoscope of the present invention.
Figure 7B:
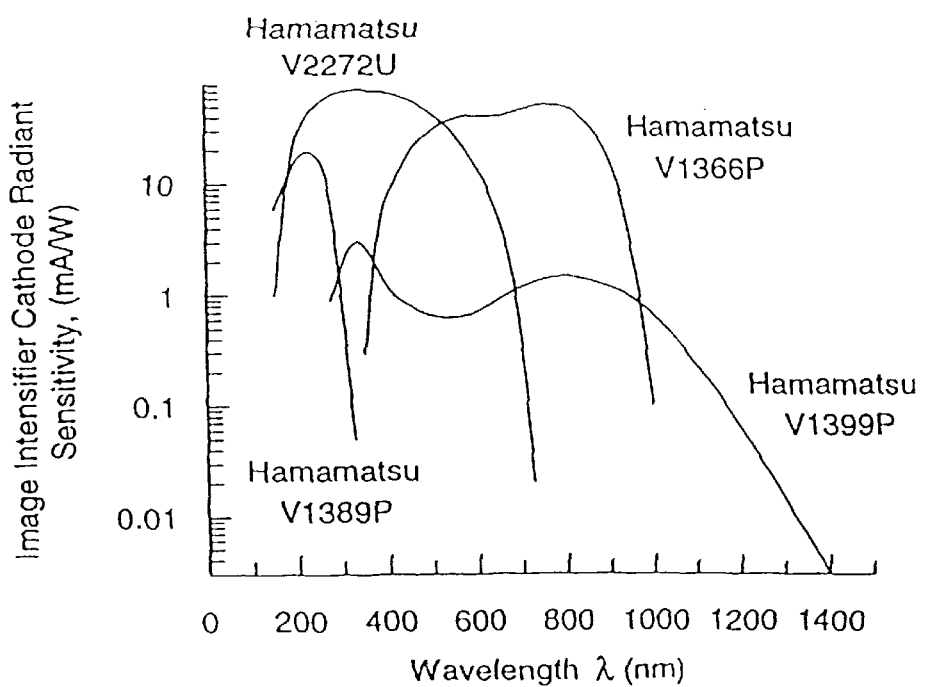

If desired, the illuminating radiation can be modulated to form a repetitive, characteristic radiation pattern that can be employed to distinguish the radiation from other possible sources of radiation having the same wavelength. Because the radiation reflected from the patient's eye is in response to the illuminating radiation, it carries the same modulation as the illuminating radiation. The reflected radiation can be demodulated by employing known techniques. FIG. 7*a* illustrates this aspect of the invention by depicting a modulating source 145g that modulates the light source 145. Such modulation can be amplitude modulation or frequency modulation of the radiation. For example, if the light source is a diode laser, modulation of the injection current can provide the desired modulation of the diode laser. The detector 270 detects the reflected radiation and provides electrical signals in response thereto. The detector 270 can be a two-dimensional array of CCD elements having sufficiently rapid response times to follow the modulation of the reflected radiation. A multiplexer 270a successively selects the output of the elements of the CCD array 270 and transmits the output signal of the selected array element to a lock-in amplifier 270b. The modulation source 145g provides the requisite reference signal for the lock-in amplifier 270b. The output of the lock-in amplifier corresponds to a de-modulated signal of the element of the array.

An alternative practice of the invention applies to a computer the output signals from the elements of the CCD array 270a, and the reference signal from the modulation source 145g. The computer executes a software program to demodulate the signals of the CCD array in a manner known in the art.

Referring again to FIG. 3, visible displays 285, 285' photoelectrically convert the aerial image taken through lenses 265, 265' by means of imaging sensor 270, 270' and display images thereof on a display in accordance with such a photoelectric conversion. Where camera tubes or CCDs are used to convert the optical image into an electrical signal which represents the light intensities present in the optical image focused on the tube, the resulting display is a video image. Image tubes, such as image intensifiers, of course do not typically produce a video image. Rather, the fluorescent screen of the image intensifier directly displays the image to the observer without first converting the optical image into an electrical signal.

Color LCDs of approximately ⅓–¾" diameter having, for example, a 0.01 mm dot pitch may be used and may be purchased from various manufacturers. Alternatively, monochrome LCDs as well as CRTs of similar dimensions may also be used, which are relatively less expensive than color LCDs. One practice of the invention employs CRTs that are preferably about 80 mm or less in length. Such CRTs are widely sold by different manufacturers. In addition to visible displays 285, 285', a television monitor 290 may also be connected to at least one of the imaging sensors so as to display the fundus image for teaching purposes.

In the case of LCDs, on the back surface thereof there are provided preferably with back lights to illuminate the LCDs. Ocular lens 295, 295' may be used to expand the visible fundus images to a desired magnification, typically 5×or less. Ocular eyepieces 295, 295' may be movable along the optical axis a few millimeters, for example, by rotating a collar (not shown) so as to compensate for ametropia in the observer. Each of the ocular lenses 295, 295' provides a virtual image of the visible display image of the fundus image, preferably at or near infinity so that a normal relaxed eye can comfortably view it. Each virtual image, however, is along a different viewing axis.

The practice of the invention can employ various types of ocular lenses, such as Huygens, Ramsden, Kellner, Plossl, or Erfle eyepiece, which are all well known in the art. Simple magnifiers may also be used, such as doublets, and triplets. See, for example, *Military Standardization Handbook—Optical Design*, MIL-HDBK-141. Erfle eyepieces may be preferable since they are well corrected for most aberrations and have a comfortable eye relief.

Those skilled in the art will readily understand that ocular lenses 295, 295' are used to view and preferably magnify the fundus images displayed on visible displays 285, 285'. The distance of the patient's eye to ophthalmoscopic lens 170 will depend upon the power thereof, but will generally be in the range of about 25 to 50 cm. Also, for optimum stereopsis, the images of the imaging sensors must be separated from each other as far as possible while falling within the pupil of the eye to be examined, as depicted in FIG. 5. Furthermore, the image representing the light source should also strike the pupil of the eye and should be separated as far as possible from the images representing the imaging sensors so as to minimize unwanted reflections along the viewing axes of the ophthalmoscope. For polarized radiation, such as radiation from a laser, polarizing filters, however, may be employed to minimize any specular reflection off the cornea.

The binocular indirect ophthalmoscope of the present invention offers several advantages over prior art ophthalmoscopes. One such advantage is that the ophthalmoscope of the invention not only allows direct viewing of retinal images as binocular images, but it also acquires the images electro-optically. This allows storage of the images in a video format, as well as allowing real-time processing of the images. That is, well known digital image processing techniques may be used to delineate and enhance desired features of the fundus image in real-time. For example, signal processors 300, 300' may be optionally used to process video images from imaging sensors 270, 270', if available, and then display the enhanced images via displays 285, 285' in real-time. That is, by properly manipulating the appearance of the image, specific features become more visible to the observer. A further alternative practice of the invention stores the electro-optical images on a computer that is equipped with suitable image processing software for selected manipulation of the images, such as enhancing the acquired images according to known image enhancement techniques.

Figure 7C:
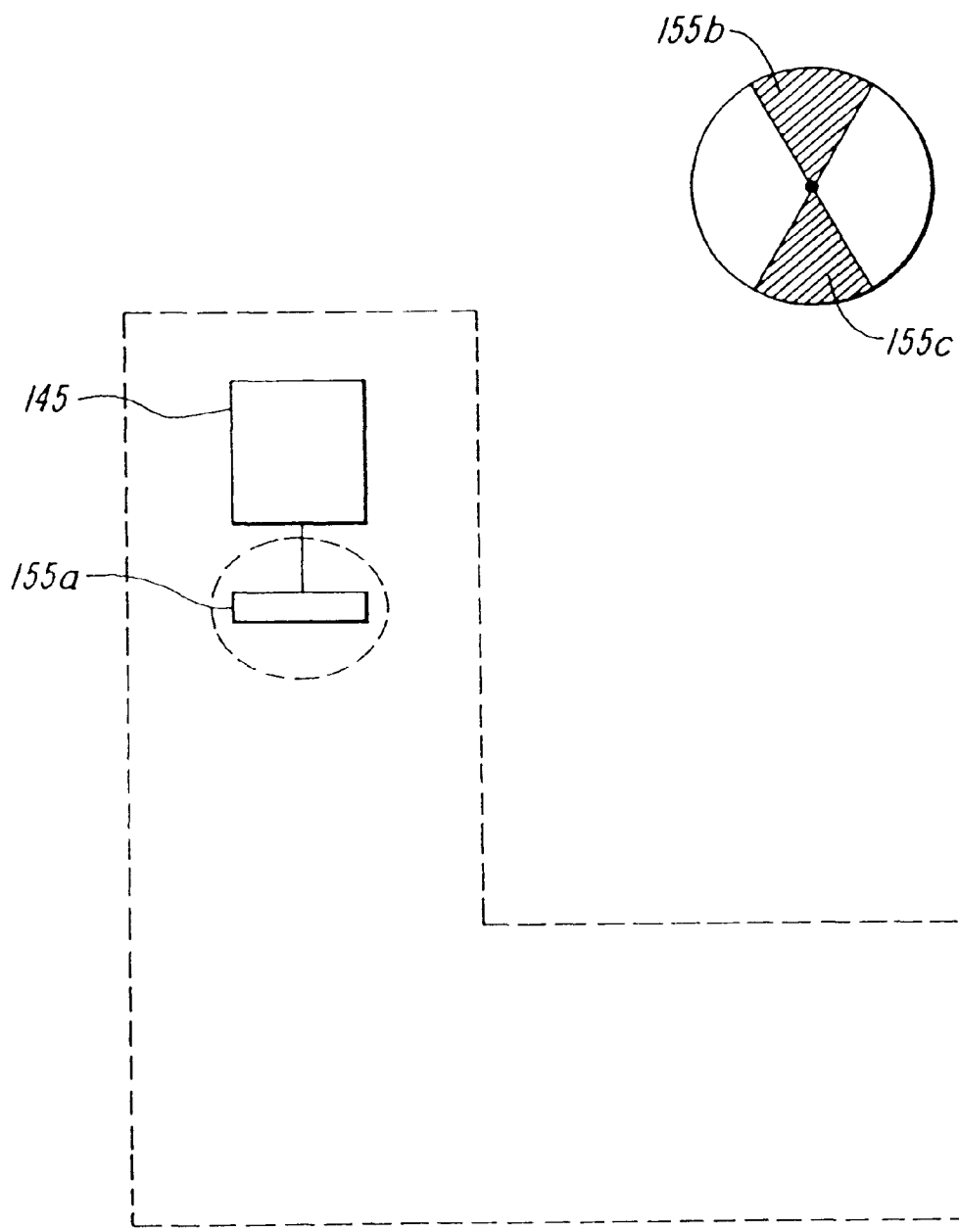
FIG. 7c is a schematic plan view of a portion of a binocular indirect ophthalmoscope according to the invention which employs filters to obtain images of the same portion of the subject's retina at a number of different wavelengths.
Figure 7D:
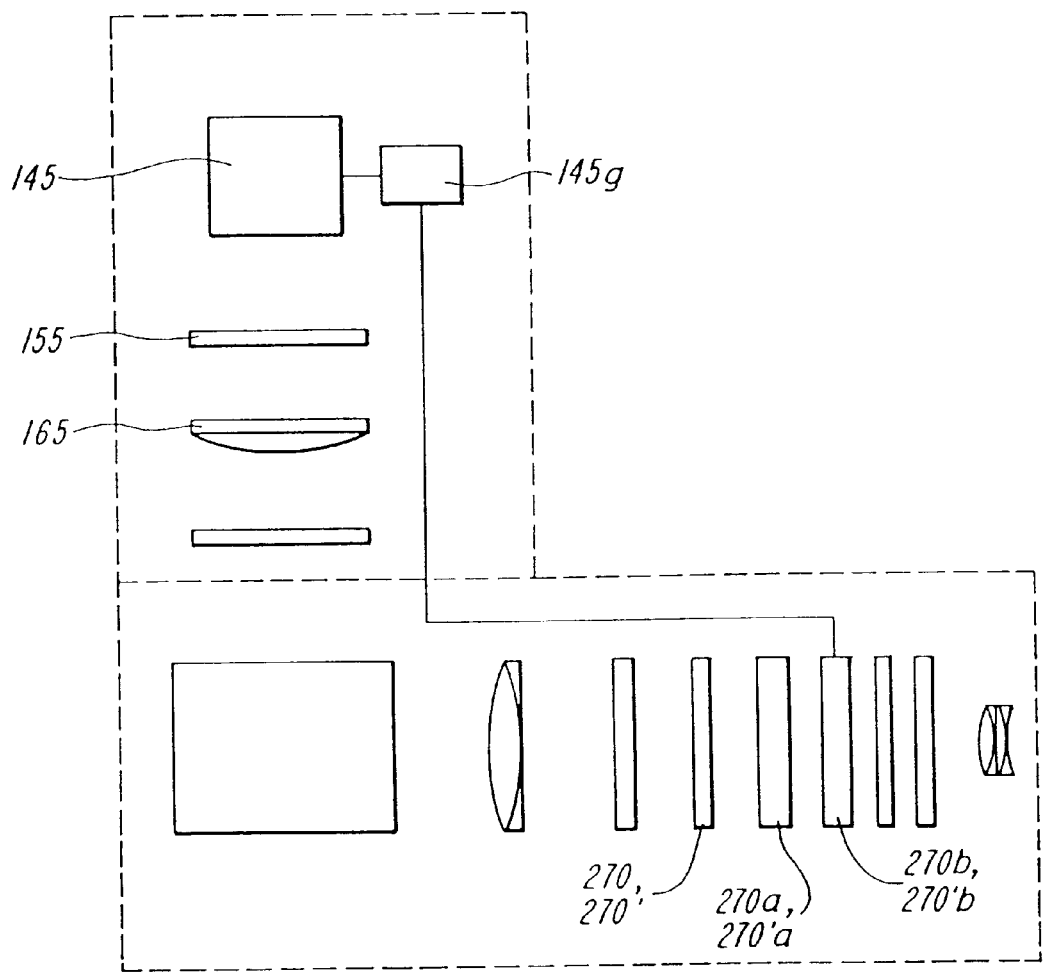
FIG. 7d is a schematic plan view of the illumination and the detection assemblies of a direct ophthalmoscope according to the invention which employs a pulsed radiation source and a coherent detector to obtain images of the subject's retina.

Another aspect of the invention relates to obtaining images of the subject's retina by illuminating the retina at different wavelengths. In particular, one practice of the invention illuminates the same portion of the retina at a plurality of wavelengths, and acquires a separate electro-optical image for each illuminating wavelength. Such images can be selectively added to each other, or subtracted from each other, to provide selected differential or other additive structural information regarding the subject's retina. FIG. 7c illustrates this aspect of the invention in more detail. In particular, reference to FIG. 7c shows a filter wheel 155a, disposed in front of the light source 145, and having two filters 155b and 155c thereon. Each filter 155b and 155c allows transmission of light having a particular wavelength. For example, the filter 155a can be selected to allow transmission of visible light having a wavelength in the blue portion of the spectrum, and the filter 155b can be selected to allow transmission of visible light having a wavelength in the red portion of the spectrum. The filter wheel can be rotated, either manually or by a motor (not shown), to illuminate the same portion of the subject's retina alternatively with radiation having blue and red wavelengths. Signal-processing electronics can subtract or otherwise compare the intensity of an image obtained when the retina is illuminated by the blue light relative to the intensity of the image obtained by the red light to attain information regarding the subject's inner retinal thickness. If the filters 155b and 155c are selected to transmit blue and green light, respectively, a difference function of the images obtained by employing each filter can provide information regarding the subject's inner retinal thickness. An alternative embodiment of the invention rapidly displays the two images, obtained with different wavelengths of light, on a monitor screen to produce a image that approximately correlates with the retinal thickness and/or concavities.

One practice of the invention illuminates the same portion of the subject's retina by infrared radiation having two different wavelengths. Subsequently, each electro-optical image, obtained in response to the illuminating radiation, is assigned a distinct color. For example, one image is visually depicted by employing the color red, while the other image is depicted by employing the color green. Such coloring of the images obtained by infrared illumination of the subject's retina is herein termed pseudo-coloring. The pseudo-colors enhance the contrast between the two images, thus allowing better visualization of the retina. For example, such depiction of two infrared images of the same portion of the retina can allow visualization of lesions that may not be readily observable in absence of pseudo-coloring of the electro-optical images.

The invention can also employ pattern recognition and other digital image processing techniques to delineate fundus features in normal and diseased eyes, such as hemorrhages, exudates, scars, and the like. Digital image processing techniques include contrast enhancement, edge enhancement, noise reduction, scaling, rotating, and pseudo-coloring the fundus image, which are all well known in the art. See, for example, *Digital Image Processing* by Pratt, John Wiley & Sons, (New York 1978). One particular advantage of such image processing techniques, is the ability to provide electronically a non-inverted image to the observer without using bulky optics in the viewing assembly to do so. Also, the fundus image maybe zoomed independently of the power of ophthalmoscopic lens 170 by accordingly processing the video images from imaging sensors 270, 270', which processing may be performed in real-time.

Those skilled in the art will readily recognize that signal processors 300, 300' may include a micro-processor based device, A/D converters, control logic, software and other associated electronics. The construction of such devices is well known in the art and hence will not be discussed herein.

Figure 8A:
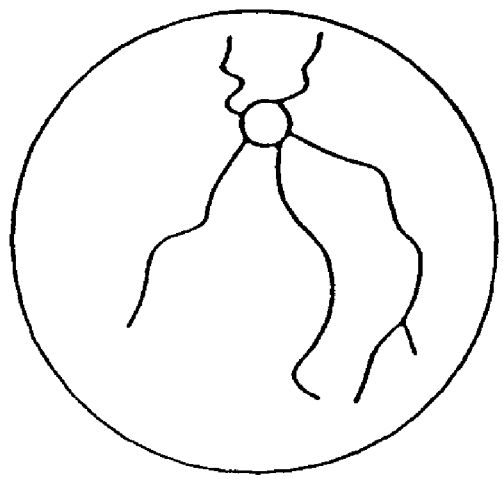
FIGS. 8(a) and (b) depict illustrative views of the fundus image along a single viewing axis under visible and infrared illumination, respectively.
Figure 8B:
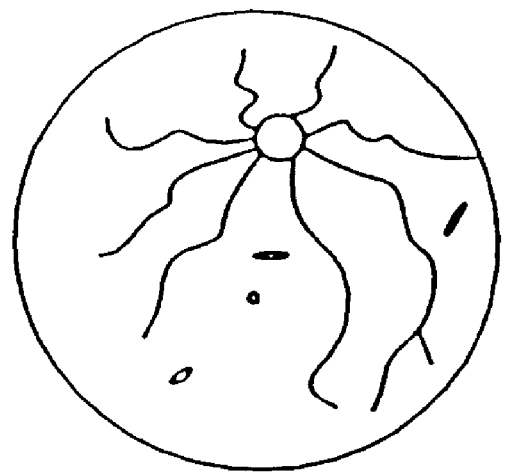

It should be clearly understood that the fundus image of the patient's eye is captured by the imaging sensors and preferably visibly displayed as a binocular image to the observer regardless of the wavelength of illumination chosen. For example using CCDs or image intensifiers, the infrared images of the fundus are converted to the visible part of the spectrum. Furthermore, proximity focused type image intensifiers may be used to generate non-inverted fundus images. FIGS. 8(a)–(b) depict illustrative views (monocular) by the observer under visible and infrared illumination, respectively, uniformly impinging on the fundus. FIG. 8(b) illustrates the enhancement of the fundus features, particularly higher contrast and resolution, when illuminated by near infrared illumination. Such an illumination may also be desirable since the patient's pupil does not react to infrared light, thereby obviating the need to dilate the patient's pupil.

It may be also desirable to have a reticule or grid electronically displayed to the observer and aligned with the center of the viewing axis. This may be readily accomplished using the digital image processing capabilities of signal processor 300, 300' which can superimpose any desired image, such as reticules, grids, scales as well as previously recorded fundus images and the like.

Figure 9:
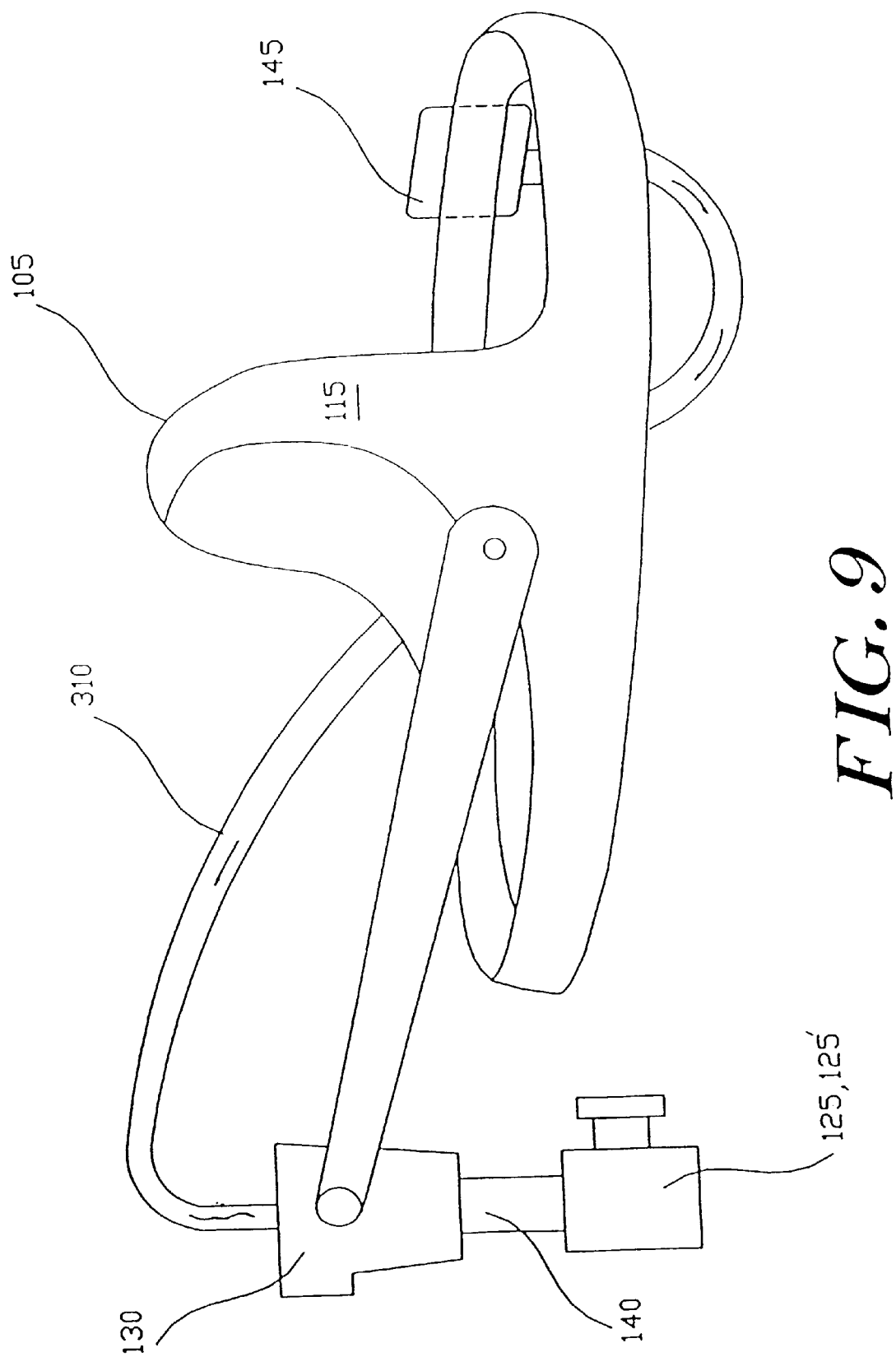
FIG. 9 is a plan elevation view of an alternative embodiment of the binocular indirect ophthalmoscope in accordance with the principles of the invention.

Alternatively, the present binocular indirect ophthalmoscope may use an optical fiber bundle 310 to guide or direct the illumination radiation from light source 145 to illumination assembly 130, as illustrated in FIG. 9. In this latter embodiment, the light source 145 may be located external to illumination assembly 130. For example, light source 145 may be secured to the head assembly 105 in any suitable manner, such as near the rear of head band 110 or located within a housing several feet away. In the latter case, this results in a generally lightweight construction for the ophthalmoscope and further adds to the reduction of strain placed on the user.

Figure 10:
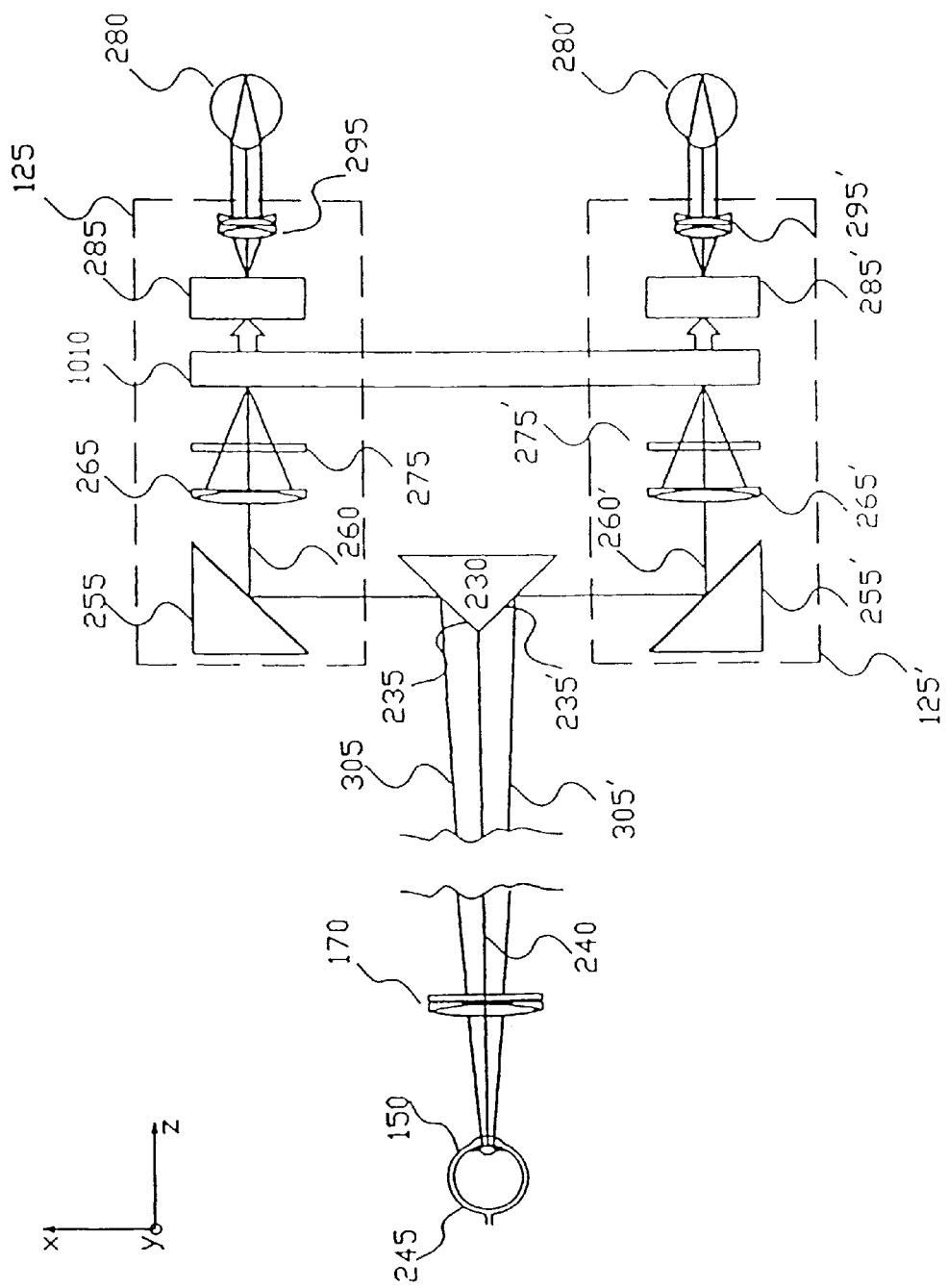
FIG. 10 is a schematic plan view of the viewing assembly of another embodiment of a binocular indirect ophthalmoscope in accordance with the principles of the present invention.

FIG. 10 illustrates another embodiment of the present invention, which is similar to the first embodiment and in which one rather than two imaging sensors is used. Similarly, mirrors 255, 255' focus on a single imaging sensor 1010 two independent non-overlapping images of the fundus of the patient's eye. It should be clearly understood that these images are still taken along two different viewing axes 305, 305' so as to permit stereoscopic viewing. Likewise, visible displays 285, 285' photoelectrically covert the non-overlapping fundus images and display images thereof to the observer through suitable ocular eyepieces. It is contemplated that the use of a single imaging sensor may be more cost effective due to today's high cost of CCDs and image intensifiers. Furthermore, a single viewing display may be used, so long as two separate images taken along different viewing axes are displayed to the observer.

The present ophthalmoscope can also be employed to observe the subject's eye without utilizing an external radiation source. For example, the ophthalmoscope of FIG. 2 without the light source 145 can image the infrared radiation that the subject's retina natually emanates. In particular, the regions of the retina having increased metabolic activities release more infrared radiation than other areas. Thus, imaging the naturally emitting infrared radiation and color coding the detected radiation according to intensity can provide retinal topography.

It should be understood that various other modifications will be readily apparent to those skilled in the art without departing from the scope and spirit of the present invention. For example, the electro-optic imaging and display system of the present invention may be used in direct ophthalmoscopes. Accordingly, it is not intended that the scope of the claims appended hereto be limited to the description set forth herein, but rather than the claims be construed as encompassing all the features of the patentable novelty that reside in the present invention, including all features that would be treated as equivalents thereto by those skilled in the art to which this invention pertains.

Having described the invention, what is new and protected by Letters Patent is:

1. An ophthalmoscope comprising:
    a light source for illuminating the interior of a patient's eye with radiation, and
    imaging devices for electro-optically imaging and displaying images of the interior of the patient's eye to an observer, said images being formed from radiation reflected from the interior of the patient's eye in response to said illuminating radiation and directed along two different optical paths.

2. The ophthalmoscope of claim 1, further including an optical fiber coupled to said light source for directing light to the interior of the patient's eye.

3. The ophthalmoscope of claim 1, further comprising a viewing assembly for receiving the radiation reflected from the interior of the patient's eye and for directing a portion of said reflected radiation along said two different optical paths to said imaging devices.

4. The ophthalmoscope of claim 3, further including a first filter disposed between said light source and the patient's eye and a second filter disposed between the patient's eye and the viewing assembly, wherein said first filter transmits radiation having a wavelength suitable for excitation of a fluorescent dye applied to the patient's eye and said second filter transmits radiation having a wavelength corresponding to the fluorescence wavelength of said dye.

5. The ophthalmoscope of claim 1, further comprising a fixation target having a selected image thereon disposed between said illuminating means and the patient's eye, thereby projecting said image onto the patient's retina.

6. The ophthalmoscope of claim 5, wherein said fixation target comprises an image former.

7. The ophthalmoscope of claim 1, further comprising a filter for selectively filtering a predetermined spectrum of the radiation from said light source.

8. The ophthalmoscope of claim 1, further comprising a fixation target having a selected image thereon disposed between said light source and the patient's eye, thereby projecting said image onto the patient's retina.

9. The ophthalmoscope of claim 8, wherein said dye is excited by radiation in the near infrared region of the electromagnetic spectrum.

10. The ophthalmoscope of claim 9, wherein said dye comprises a fluorescein dye excitable by radiation having a wavelength in the blue portion of the spectrum, said dye fluorescing in the green portion of the spectrum upon excitation.

11. The ophthalmoscope of claim 1, further including a filter assembly comprising a plurality of filters disposed between said light source and the patient's eye to generate the image of a portion of the patient's retina at a plurality of wavelengths corresponding to transmission wavelengths of said filters.

12. The ophthalmoscope of claim 1, further including a wavelength varying mechanism for successively illuminating a portion of the subject's retina by infrared radiation having two different wavelengths to obtain two electro-optical images wherein each image corresponds to a different one of said wavelengths.

13. The ophthalmoscope of claim 12, wherein each of said images is visually depicted by employing a distinct color, thereby increasing the contrast between the images.

14. The ophthalmoscope of claim 12, wherein said wavelength varying mechanism comprises two infrared sources having different radiation wavelengths.

15. The ophthalmoscope of claim 1, further comprising a filter for selectively filtering a predetermined spectrum of the radiation from said light source.

16. The ophthalmoscope of claim 15, wherein said predetermined spectrum includes the infrared spectrum.

17. The ophthalmoscope of claim 15, wherein said predetermined spectrum includes the visible spectrum.

18. The ophthalmoscope of claim 1, further comprising a filter for selectively filtering a predetermined spectrum of the reflected light from the interior of the patient's eye.

19. The ophthalmoscope of claim 18, wherein said predetermined spectrum includes the infrared spectrum.

20. The ophthalmoscope of claim 18, wherein said predetermined spectrum includes the visible spectrum.

21. The ophthalmoscope of claim 1, wherein said light source includes an infrared source.

22. The ophthalmoscope of claim 1, wherein said light source includes a visible light source.

23. The ophthalmoscope of claim 1, wherein said light source includes a laser.

24. The ophthalmoscope of claim 1, wherein said imaging devices include a CCD.

25. The ophthalmoscope of claim 1, wherein said imaging devices include a LCD.

26. The ophthalmoscope of claim 1, wherein said imaging devices include a CRT.

27. The ophthalmoscope of claim 1, wherein said imaging devices include a camera tube.

28. The ophthalmoscope of claim 1, wherein said imaging devices include an image tube.

29. The ophthalmoscope of claim 28, wherein said image tube is an image intensifier.

30. The ophthalmoscope of claim 1, further comprising a processor for processing said images of the interior of the patient's eye.

31. An improved ophthalmoscope, the improvement comprising:
a radiation source for illuminating the interior of a patient's eye, and
imaging devices for electro-optically converting non-visible radiation reflected from the interior of the patient's eye in response to said illuminating radiation to a binocular visible display thereof.

32. The improved ophthalmoscope of claim 31, further including an optical fiber coupled to said radiation source for directing light to the interior of the patient's eye.

33. The improved ophthalmoscope of claim 31, further comprising a viewing assembly for receiving the radiation reflected from the interior of the patient's eye and for directing a portion of said reflected radiation along two different optical paths to said imaging devices.

34. The improved ophthalmoscope of claim 31, further comprising a filter for selectively filtering a predetermined spectrum of the radiation from said radiation source.

35. The improved ophthalmoscope of claim 34, wherein said predetermined spectrum includes the infrared spectrum.

36. The improved ophthalmoscope of claim 34, wherein said predetermined spectrum includes the visible spectrum.

37. The improved ophthalmoscope of claim 31, further comprising a filter for selectively filtering a predetermined spectrum of the reflected radiation from the interior of the patient's eye.

38. The improved ophthalmoscope of claim 37, wherein said predetermined spectrum includes the infrared spectrum.

39. The improved ophthalmoscope of claim 37, wherein said predetermined spectrum includes the visible spectrum.

40. The improved ophthalmoscope of claim 31, wherein said radiation source is an infrared light source.

41. The improved ophthalmoscope of claim 31, wherein said radiation source is a visible light source.

42. The improved ophthalmoscope of claim 31, wherein said imaging devices include a CCD.

43. The improved ophthalmoscope of claim 31, wherein said imaging devices include a LCD.

44. The improved ophthalmoscope of claim 31, wherein said imaging devices include a CRT.

45. The improved ophthalmoscope of claim 31, wherein said imaging devices include an image camera.

46. The improved ophthalmoscope of claim 31, wherein said imaging devices include an image tube.

47. The improved ophthalmoscope of claim 46, wherein said image tube in an image intensifier.

48. The improved ophthalmoscope of claim 31, further comprising a processor for processing the image corresponding to the binocular visible display of the interior of the patient's eye.

49. A binocular ophthalmoscope comprising
a light source for illuminating the interior of a patient's eye with light of a desired spectrum,
a viewing assembly for receiving light reflected from the interior of the patient's eye in response to said illuminating light and directing along two optical paths a portion of said reflected light,
first and second imaging sensors, each of said sensors being placed in a different one of the two optical paths,
first and second lenses for focusing said portion of said reflected light onto said first and second imaging sensors, respectively, whereby said first and second imaging sensors produce first and second electrical signals, respectively in response to said focused reflected light, and first and second displays responsive to said first and second electrical signals, respectively, for converting said first and second electrical signals into first and second visible display images of the interior of the patient's eye, said visible display images being associated with the images of the interior of the patient's eye taken along said two optical paths.

50. The binocular ophthalmoscope of claim 49, wherein said light source includes an infrared source of radiation.

51. The binocular ophthalmoscope of claim 49, wherein said light source includes a visible source of radiation.

52. The binocular ophthalmoscope of claim 49, further comprising a filter for selectively transmitting a predetermined spectrum of the light from said light source.

53. The binocular ophthalmoscope of claim 52, wherein said predetermined spectrum is in the visible spectrum.

54. The binocular ophthalmoscope of claim 52, wherein said predetermined spectrum is in the infrared spectrum.

55. The binocular ophthalmoscope of claim 49, further including an intensity modifier for adjusting the intensity of said light with a desired spectrum.

56. The binocular ophthalmoscope of claim 49, wherein said viewing assembly includes a pair of reflective elements spaced apart perpendicular to the direction in which the reflected light from the patient's eye is propagating.

57. The binocular ophthalmoscope of claim 49, wherein said first and second imaging sensors are CCDs.

58. The binocular ophthalmoscope of claim 49, wherein said first and second imaging sensors are image cameras.

59. The binocular ophthalmoscope of claim 49, wherein said displays are LCDs.

60. The binocular ophthalmoscope of claim 49, wherein said displays are CRTs.

61. The binocular ophthalmoscope of claim 49, further comprising a filter for selectively filtering a predetermined spectrum of the light reflected from the interior of the patient's eye.

62. The binocular ophthalmoscope of claim 49, further comprising a processor for signal processing said first and second electrical signals.

63. An indirect ophthalmoscope comprising a light source for illuminating the interior of a patient's eye with light, an image intensifier having a fluorescent screen and a photosensitive surface, said fluorescent screen reproducing thereon an image corresponding to that formed on the photosensitive surface by light being focused on said surface, and a lens for focusing on said photosensitive surface an image of an aerial image of the patient's eye formed from light being reflected from the interior of the patient's eye in response to said illuminating light.

64. The ophthalmoscope of claim 63, wherein said image intensifier converts non-visible radiation incident on the photosensitive surface to a visible display on the fluorescent screen.

65. The ophthalmoscope of claim 63, wherein the non-visible radiation is infrared radiation.

66. The ophthalmoscope of claim 63, further including an optical fiber coupled to said light source for directing light to the interior of the patient's eye.

67. The ophthalmoscope of claim 63, further comprising a filter for selectively filtering a predetermined spectrum of the light from said light source.

68. The ophthalmoscope of claim 63, further comprising a filter for selectively filtering a predetermined spectrum of the reflected light from the interior of the patient's eye.

69. The ophthalmoscope of claim 63, wherein said light source includes an infrared light source.

70. The ophthalmoscope of claim 63, wherein said light source includes a visible light source.

71. An ophthalmoscope comprising a light source for illuminating the interior of a patient's eye with light, first and second image intensifiers, each having a fluorescent screen and a photosensitive surface, each fluorescent screen reproducing thereon an image focused on the corresponding photosensitive surface, and first and second lenses for focusing on each photosensitive surface of said first and second image intensifiers, respectively an image of the interior of the patient's eye formed from light being reflected from the interior of the patient's eye in response to said illuminating light, each of said images of the interior of the patient's eye taken along two different optical paths.

72. The ophthalmoscope of claim 71, wherein each of said first and second image intensifiers converts non-visible radiation incident on the photosensitive surface to a visible display on the fluorescent screen.

73. The ophthalmoscope of claim 71, wherein the non-visible radiation is infrared radiation.

74. The ophthalmoscope of claim 71, further including an optical fiber coupled to said light source for directing light to the interior of the patient's eye.

75. The ophthalmoscope of claim 71, further comprising a filter for selectively filtering a predetermined spectrum of the light from said light source.

76. The ophthalmoscope of claim 71, further comprising a filter for selectively filtering a predetermined spectrum of the reflected light from the interior of the patient's eye.

77. The ophthalmoscope of claim 71, wherein said light source includes an infrared light source.

78. The ophthalmoscope of claim 71, wherein said light source includes a visible light source.

* * * * *